(12) United States Patent
Wadman

(10) Patent No.: US 7,248,368 B2
(45) Date of Patent: Jul. 24, 2007

(54) SCATTEROMETER AND A METHOD FOR INSPECTING A SURFACE

(75) Inventor: Sipke Wadman, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 160 days.

(21) Appl. No.: 10/546,313

(22) PCT Filed: Feb. 18, 2004

(86) PCT No.: PCT/IB2004/050125

§ 371 (c)(1),
(2), (4) Date: Aug. 19, 2005

(87) PCT Pub. No.: WO2004/077033

PCT Pub. Date: Sep. 10, 2004

(65) Prior Publication Data

US 2006/0066862 A1    Mar. 30, 2006

(30) Foreign Application Priority Data

Feb. 28, 2003    (EP) .................................. 03100511

(51) Int. Cl.
*G01N 21/47*    (2006.01)
*G01B 11/30*    (2006.01)

(52) U.S. Cl. ..................................... 356/446; 356/600
(58) Field of Classification Search ........ 356/445–446, 356/600
See application file for complete search history.

(56) References Cited

U.S. PATENT DOCUMENTS 5,880,843 A    3/1999    Hermosillo-Valadez et al.

FOREIGN PATENT DOCUMENTS

| DE | 3731171 A | 3/1989 |
| DE | 19954183 | 5/2001 |
| JP | 60228910 | 11/1985 |

*Primary Examiner*—Gregory J. Toatley, Jr.
*Assistant Examiner*—Amanda Merlino

(57) ABSTRACT

A scatterometer comprising a source (2) for providing an incident radiation beam (1) to be directed to the surface of a sample (4), and means for directing said incident radiation beam (1) at different angles towards the surface of the sample (4). The scatterometer furthermore comprising a screen (6) for receiving the reflection (7) of the incident radiation beam (1), and a camera (9) for recording the scatter profile (7) as projected on said screen (6) by the reflected radiation beam (5). The scatterometer is provided with means (11,12,13,14,15) for moving the screen (6) and thereby keeping it in the reflected radiation beam (5), and with means for keeping the camera (9) directed to the moving screen (6).

7 Claims, 1 Drawing Sheet

SCATTEROMETER AND A METHOD FOR INSPECTING A SURFACE

Figure 1:
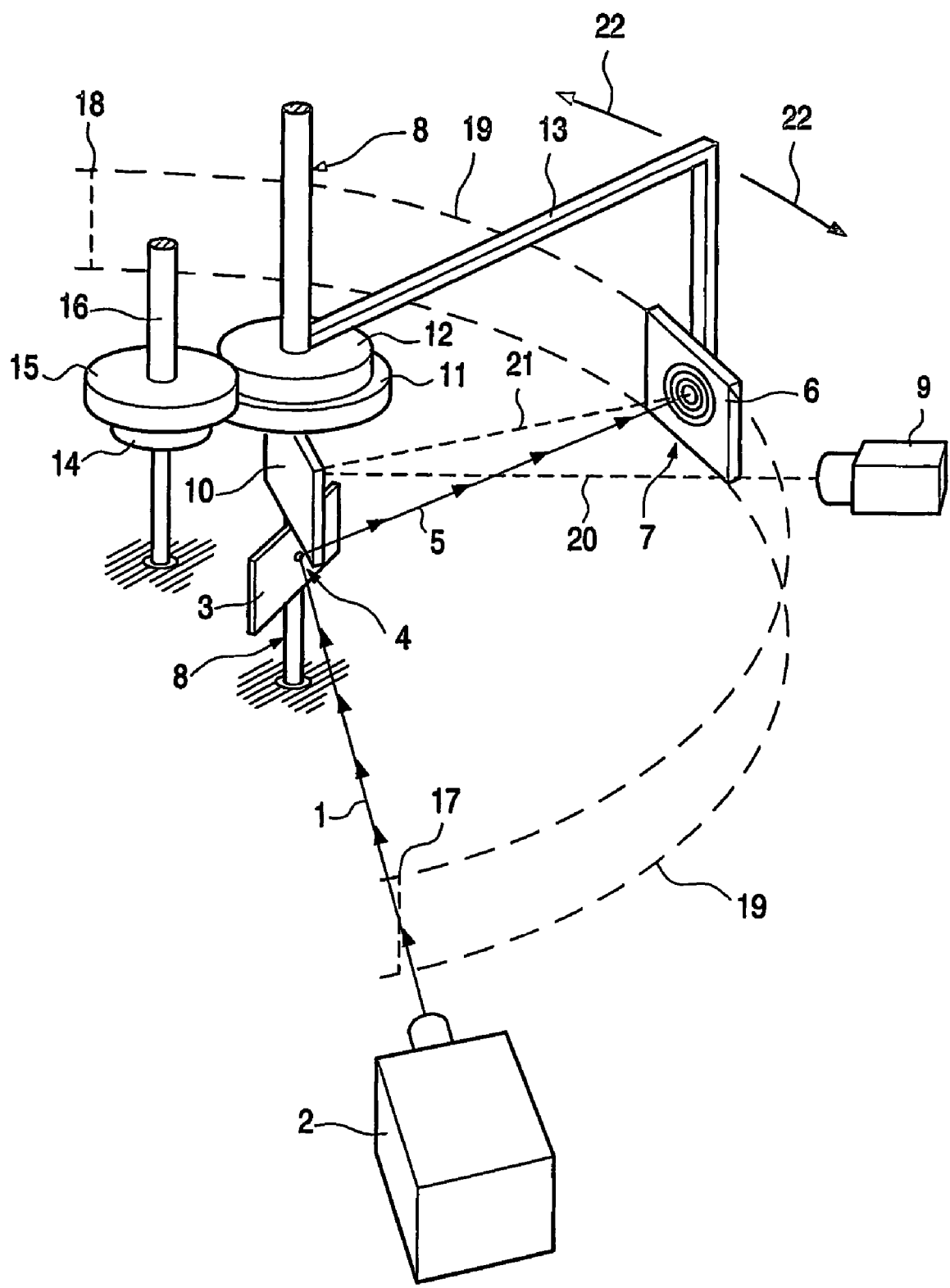

The invention is related to a specular reflection meter, known as scatterometer, comprising a source for providing an incident radiation beam to be directed to the surface of a sample, means for directing said incident radiation beam at different angles towards the surface of the sample, a screen for receiving the reflection of the incident radiation beam, and a camera for recording the scatter profile as projected on the screen by the reflected radiation beam.

Many surfaces of industrial products have a physical structure with certain properties as to enhance the functionality of the product or to improve its appearance. A few typical examples are the extreme smooth surfaces of high quality optical components, wear resistant layers on cutting tools, the surface of paints, the fine texture of plastic parts, the pressing of rolling textures produced in sheet metal, and the high gloss metallic-looking lacquers for the automotive industry. The surface structure and the quality of such surfaces can be assessed by a scatterometer, whereby an incident radiation beam, for example a light beam, is directed to the surface to be analyzed and the reflection of such beam is projected on a screen, so that a scatter profile appears on that screen.

A scatterometer is disclosed in WO-A-00/37923, whereby the screen is formed by the internal surface of a spherical dome, and the sample is located in the center of the dome. The source for providing the incident radiation beam is located outside said dome and the incident radiation beam enters the dome through an aperture in the dome, which aperture has the shape of a meridian slot, so that the beam can be directed at different angles to the surface of the sample. The scatter profile is projected on the concave internal surface of the dome, which internal surface forms the screen. A camera is located outside the dome and observes the scatter profile through an aperture in the dome and through a mirror near the center of the dome. The mirror can be convex, so that the camera can observe a wide portion of the inside of the dome. When making use of a flat mirror a predetermined portion of the internal surface of the dome can be observed, whereby the mirror can be moved (rotate around an axis) to observe different portions of said internal surface of the dome.

The image to be recorded by the camera, i.e. the scatter profile or a portion of it, can be disturbed by so called higher order reflections. These higher order reflections are caused by the luminosity of one part of the screen that illuminates another part of the screen. Such higher order reflections may occur in case the screen has a concave shape, for example a spherical shape or a cylindrical shape. The higher the reflection coefficient of the screen is and the larger its angular extent, the more disturbing the higher order reflections are. This effect causes an illumination on top of the scatter profile that has to be determined and/or recorded. For example, the higher order reflections are very disturbing when assessing the quality of very smooth surfaces such as optical surfaces, display screens, or semiconductor wafers.

The object of the invention is to provide a scatterometer, whereby higher order reflections can be reduced, so that more accurate observation and records of the scatter profile can be made.

To accomplish with this object, the scatterometer is provided with means for moving the screen and thereby keeping it in the reflected radiation beam, and with means for keeping the camera directed to the moving screen, for example through a moving mirror. Thereby a curvature of the screen can be reduced or avoided, resulting in reduction of the higher order reflections or absence of such reflections.

Preferably, the screen is substantial flat or completely flat, whereby higher order reflections are completely avoided. The screen may be even convex, whereby higher order reflections cannot occur.

In one preferred embodiment the source for providing the incident radiation beam is mounted in a fixed position, whereby the sample can rotate around an axis substantially perpendicular with respect to the direction of said incident radiation beam. When rotating the sample, the angle at which the incident radiation beam hits the surface of the sample changes. Thereby the screen can move by rotating around substantially the same axis, whereby its angular velocity is two times the angular velocity of the sample, so that the screen will remain in the reflected radiation beam during its movement.

Preferably, the camera is mounted in a fixed position and can observe the screen through a mirror, whereby the mirror can rotate substantially around said same axis with an angular velocity similar to the angular velocity of the sample. Thereby a sample support member and said mirror may be attached to an unit rotating around said axis, whereby said screen is connected to said unit, and whereby it can rotate around said axis with a different angular velocity.

The invention is furthermore related to a method for inspecting a surface, whereby a radiation source provides an incident radiation beam being directed towards the surface of the sample at different angles, whereby a screen receives the reflected radiation beam, and whereby a camera records the scatter profile as projected on said screen. Thereby the screen is moved to keep it in the reflected radiation beam, and the camera keeps directed to the moving screen, for example through a moving mirror.

The invention will now be explained by means of a description of an embodiment of a scatterometer, in which reference is made to the drawing of FIG. 1, showing schematically—in perspective view—portions of a scatterometer. To explain the working principle, only some portions of the scatterometer are schematically shown, other portions are not shown.

The figure shows an incident light beam 1 originating from a radiation source 2 and directed to the surface of a sample 4. The radiation source 2 may generate a monochromatic radiation beam or a polychromatic radiation beam, for example white light. Sample 4 is attached to a sample support member 3, which is dull black to avoid undesired reflections, i.e. other reflections than the reflections from the surface of the sample 4. A (not shown) diaphragm in the light path of the incident radiation beam 1 can adjust the illuminated area of the surface of the sample 4. Thereby the diameter of the incident radiation beam 1 can be limited to a value between for example 2 mm and 12 mm.

The incident radiation beam 1 is reflected at the surface of the sample 4 and the reflected radiation beam 5 projects on a flat screen 6 a scatter profile 7. The screen 6 is coated with a diffuse neutral gray coating to achieve an optimal image of the projected scatter profile 7.

The scatter profile 7 on screen 6 contains information about the surface structure of the sample 4, and can be recorded by a camera 9. Camera 9 is directed to a mirror 10 and observes the scatter profile 7 on the screen 6 through said mirror 10, as indicated by dashed lines 20 and 21. (The figure shows the backside of mirror 10.)

Radiation source 2 as well as camera 9 is mounted in a fixed position. The sample support member 3 and the mirror 10 are both attached to a vertical pin 8, which pin 8 can rotate around its longitudinal (vertical) axis. Therefore, the sample support member 3 and the mirror 10 can both rotate around the said vertical axis of pin 8 as a rotating unit.

Also the screen 6 can rotate around said vertical axis of pin 8. To achieve such rotation, the screen 6 is connected by an arm 13 to tooth wheel 12, which tooth wheel 12 can rotate around pin 8. Arrows 22 indicate the movement of arm 13, and dashed lines 19 indicate the movement of screen 6.

The angle at which the incident radiation beam 1 hits the surface of the sample 4 can be changed by rotating pin 8, so that the sample support member 3 rotates around the vertical axis of pin 8. Because the radiation source 2 is mounted at a fixed position, the reflection 5 of the incident radiation beam 1 is rotating with an angular velocity that is two times the angular velocity of the sample support member 3. Therefore, to receive the projected scatter profile 7, the screen 6 has to rotate around the vertical axis of pin 8 with an angular velocity which is two times the angular velocity of pin 8 itself, with attached to it the sample support member 3.

Such difference in angular velocity can be achieved in many ways. According to the embodiment shown in the figure it is achieved by a simple toothed wheel mechanism. A first toothed wheel 11 is connected to pin 8. Toothed wheel 11 is in engagement with a second toothed wheel 14, having half the number of teeth, so that the angular velocity of toothed wheel 14 is two times the angular velocity of toothed wheel 11 and pin 8. A third toothed wheel 15 is mounted on the same vertical pin 16 on which toothed wheel 14 is mounted, and it rotates with the same angular velocity as toothed wheel 14. Toothed wheel 14 is in engagement with a fourth toothed wheel 12 on which arm 13 is mounted. Toothed wheel 12 can rotate around pin 8 and will also have an angular velocity of two times the angular velocity of pin 8, since toothed wheel 15 and toothed wheel 12 have the same number of teeth.

It will be clear from the FIGURE that by rotating the sample support member 3 over 90°, the screen 6 will rotate over 180°, as indicated by the dashed lines 17, 18 and 19, whereby the scatter profile 7 is constantly projected on screen 6. The camera 9 has a fixed position and is directed to mirror 10, as is indicated by dashed line 20. Because mirror 10 rotates together with support member 3, the camera will constantly observe the screen 6, as is indicated by dashed line 21.

The described embodiment of the scatterometer is merely an example; a great many other embodiments are possible.

The invention claimed is:

1. A scatterometer comprising a source for providing an incident radiation beam to be directed to the surface of a sample, means for directing said incident radiation beam at different angles towards the surface of the sample, a screen for receiving the reflection of the incident radiation beam, and a camera for recording the scatter profile as projected on said screen by the reflected radiation beam, characterized by means for moving the screen and thereby keeping it in the reflected radiation beam, and by means for keeping the camera directed to the moving screen.

2. A scatterometer as claimed in claim 1, characterized in that the screen is substantial flat.

3. A scatterometer as claimed in claim 1, characterized in that the source for providing an incident radiation beam is mounted in a fixed position and in that the sample can rotate around an axis substantial perpendicular with respect to the direction of said incident radiation beam.

4. A scatterometer as claimed in claim 3, characterized in that the screen can rotate around substantially the same axis, whereby its angular velocity is two times the angular velocity of the sample.

5. A scatterometer as claimed in claim 3, characterized in that the camera is mounted in a fixed position and can observe the screen through a mirror, whereby the mirror can rotate substantially around said same axis with an angular velocity similar to the angular velocity of the sample.

6. A scatterometer as claimed in claim 5, characterized in that a sample support member and said mirror are attached to an unit rotating around said axis, whereby said screen is connected to said unit, whereby it can rotate around said axis with a different angular velocity.

7. A method for inspecting a surface, whereby an radiation source provides an incident radiation beam being directed towards the surface of a sample at different angles, whereby a screen receives the reflected radiation beam, and whereby a camera records the scatter profile as projected on said screen, characterized in that the screen is moved to keep it in the reflected radiation beam, and in that the camera is kept directed to the moving screen.

* * * * *